United States Patent
Rudnitsky et al.

(10) Patent No.: US 12,042,124 B2
(45) Date of Patent: Jul. 23, 2024

(54) REFLECTION SUPPRESSION USING FLUORESCENCE

(71) Applicant: Align Technology, Inc., San Jose, CA (US)

(72) Inventors: Arkady Rudnitsky, Rehovot (IL); Eliahou Franklin Nizard, Jerusalem (IL); Shlomi Buganim, Beer Sheva (IL)

(73) Assignee: Align Technology, Inc., San Jose, CA (US)

( * ) Notice: Subject to any disclaimer, the term of this patent is extended or adjusted under 35 U.S.C. 154(b) by 858 days.

(21) Appl. No.: 17/074,439

(22) Filed: Oct. 19, 2020

(65) Prior Publication Data

US 2021/0121049 A1    Apr. 29, 2021

Related U.S. Application Data

(60) Provisional application No. 62/925,323, filed on Oct. 24, 2019.

(51) Int. Cl.
| *A61B 1/00* | (2006.01) |
| *A61B 1/04* | (2006.01) |
| *A61B 1/06* | (2006.01) |
| *A61B 1/24* | (2006.01) |
| *A61C 9/00* | (2006.01) |

(52) U.S. Cl.
CPC ...... *A61B 1/00142* (2013.01); *A61B 1/00009* (2013.01); *A61B 1/00059* (2013.01); *A61B 1/00096* (2013.01); *A61B 1/00105* (2013.01); *A61B 1/00108* (2013.01); *A61B 1/00135* (2013.01); *A61B 1/00194* (2022.02); *A61B 1/043* (2013.01); *A61B 1/063* (2013.01); *A61B 1/0684* (2013.01); *A61B 1/24* (2013.01); *A61C 9/0053* (2013.01)

(58) Field of Classification Search
None
See application file for complete search history.

(56) References Cited

U.S. PATENT DOCUMENTS

| 6,099,314 | A  | 8/2000  | Kopelman et al.   |
| 6,334,772 | B1 | 1/2002  | Taub et al.       |
| 6,334,853 | B1 | 1/2002  | Kopelman et al.   |
| 6,463,344 | B1 | 10/2002 | Pavlovskaia et al.|
| 6,542,249 | B1 | 4/2003  | Kofman et al.     |
| 6,633,789 | B1 | 10/2003 | Nikolskiy et al.  |
| 6,664,986 | B1 | 12/2003 | Kopelman et al.   |
| 6,697,164 | B1 | 2/2004  | Babayoff et al.   |
| 6,845,175 | B2 | 1/2005  | Kopelman et al.   |

(Continued)

*Primary Examiner* — Rebecca A Volentine
(74) *Attorney, Agent, or Firm* — Lowenstein Sandler LLP

(57) ABSTRACT

An apparatus for intraoral scanning includes an elongate handheld wand comprising a probe at a distal end of the handheld wand, one or more light projectors coupled to the handheld wand, and one or more cameras coupled to the handheld wand. Each camera comprises a camera sensor and objective optics comprising one or more lenses. Each camera is configured to focus at an object focal plane that is located between 1 mm and 30 mm from the lens that is farthest from the camera sensor. The apparatus further includes a fluorescent transparent film deposited on a surface selected from the group consisting of: a window of the probe through which light exits and enters the probe, and a transparent surface that is not integral to the probe.

30 Claims, 6 Drawing Sheets

(56) References Cited

U.S. PATENT DOCUMENTS

| | | |
|---|---|---|
| 6,847,490 B1 * | 1/2005 | Nordstrom ......... A61B 1/00142 600/407 |
| 6,979,196 B2 | 12/2005 | Nikolskiy et al. |
| 7,030,383 B2 | 4/2006 | Babayoff et al. |
| 7,202,466 B2 | 4/2007 | Babayoff et al. |
| 7,255,558 B2 | 8/2007 | Babayoff et al. |
| 7,286,954 B2 | 10/2007 | Kopelman et al. |
| 7,319,529 B2 | 1/2008 | Babayoff |
| 7,373,286 B2 | 5/2008 | Nikolskiy et al. |
| 7,507,088 B2 | 3/2009 | Taub et al. |
| 7,545,372 B2 | 6/2009 | Kopelman et al. |
| 7,698,068 B2 | 4/2010 | Babayoff |
| 7,916,911 B2 | 3/2011 | Kaza et al. |
| 8,108,189 B2 | 1/2012 | Chelnokov et al. |
| 8,244,028 B2 | 8/2012 | Kuo et al. |
| 8,587,582 B2 | 11/2013 | Matov et al. |
| 8,948,482 B2 | 2/2015 | Levin |
| D742,518 S | 11/2015 | Barak et al. |
| 9,192,305 B2 | 11/2015 | Levin |
| 9,261,356 B2 | 2/2016 | Lampert et al. |
| 9,261,358 B2 | 2/2016 | Atiya et al. |
| 9,299,192 B2 | 3/2016 | Kopelman |
| D760,901 S | 7/2016 | Barak et al. |
| 9,393,087 B2 | 7/2016 | Moalem |
| 9,408,679 B2 | 8/2016 | Kopelman |
| 9,431,887 B2 | 8/2016 | Boltanski |
| 9,439,568 B2 | 9/2016 | Atiya et al. |
| 9,451,873 B1 | 9/2016 | Kopelman et al. |
| D768,861 S | 10/2016 | Barak et al. |
| D771,817 S | 11/2016 | Barak et al. |
| 9,491,863 B2 | 11/2016 | Boltanski |
| D774,193 S | 12/2016 | Makmel et al. |
| 9,510,757 B2 | 12/2016 | Kopelman et al. |
| 9,660,418 B2 | 5/2017 | Atiya et al. |
| 9,668,829 B2 | 6/2017 | Kopelman |
| 9,675,430 B2 | 6/2017 | Verker et al. |
| 9,693,839 B2 | 7/2017 | Atiya et al. |
| 9,717,402 B2 | 8/2017 | Lampert et al. |
| 9,724,177 B2 | 8/2017 | Levin |
| 9,844,426 B2 | 12/2017 | Atiya et al. |
| 10,076,389 B2 | 9/2018 | Wu et al. |
| 10,098,714 B2 | 10/2018 | Kuo |
| 10,108,269 B2 | 10/2018 | Sabina et al. |
| 10,111,581 B2 | 10/2018 | Makmel |
| 10,111,714 B2 | 10/2018 | Kopelman et al. |
| 10,123,706 B2 | 11/2018 | Elbaz et al. |
| 10,136,972 B2 | 11/2018 | Sabina et al. |
| 10,380,212 B2 | 8/2019 | Elbaz et al. |
| 10,390,913 B2 | 8/2019 | Sabina et al. |
| 10,453,269 B2 | 10/2019 | Furst |
| 10,456,043 B2 | 10/2019 | Atiya et al. |
| 10,499,793 B2 | 12/2019 | Ozerov et al. |
| 10,504,386 B2 | 12/2019 | Levin et al. |
| 10,507,087 B2 | 12/2019 | Elbaz et al. |
| 10,517,482 B2 | 12/2019 | Sato et al. |
| 10,695,150 B2 | 6/2020 | Kopelman et al. |
| 10,708,574 B2 | 7/2020 | Furst et al. |
| 10,772,506 B2 | 9/2020 | Atiya et al. |
| 10,813,727 B2 | 10/2020 | Sabina et al. |
| 10,888,399 B2 | 1/2021 | Kopelman et al. |
| 10,952,816 B2 | 3/2021 | Kopelman |
| 10,980,613 B2 | 4/2021 | Shanjani et al. |
| 11,013,581 B2 | 5/2021 | Sabina et al. |
| 2006/0032924 A1 * | 2/2006 | Huston ............... B41J 11/00214 235/462.05 |
| 2013/0286174 A1 * | 10/2013 | Urakabe ................. A61B 1/04 348/66 |
| 2014/0212832 A1 * | 7/2014 | Fisker ...................... G06T 7/55 433/29 |
| 2015/0238072 A1 * | 8/2015 | Makmel ................ A61B 1/253 219/221 |
| 2018/0299792 A1 * | 10/2018 | Bearda ................ G03F 7/70308 |
| 2019/0029784 A1 | 1/2019 | Moalem et al. |
| 2019/0379881 A1 * | 12/2019 | Tewes ................ G02B 19/0014 |
| 2019/0388193 A1 | 12/2019 | Saphier et al. |
| 2019/0388194 A1 | 12/2019 | Atiya et al. |
| 2020/0281700 A1 | 9/2020 | Kopelman et al. |
| 2020/0281702 A1 | 9/2020 | Kopelman et al. |
| 2020/0315434 A1 | 10/2020 | Kopelman et al. |
| 2020/0349698 A1 | 11/2020 | Minchenkov et al. |
| 2020/0349705 A1 | 11/2020 | Minchenkov et al. |
| 2020/0404243 A1 | 12/2020 | Saphier et al. |
| 2021/0030503 A1 | 2/2021 | Shalev et al. |
| 2021/0059796 A1 | 3/2021 | Weiss et al. |
| 2021/0068773 A1 | 3/2021 | Moshe et al. |

* cited by examiner

REFLECTION SUPPRESSION USING FLUORESCENCE

RELATED APPLICATIONS

This patent application claims the benefit under 35 U.S.C. § 119(e) of U.S. Provisional Application No. 62/925,323, filed Oct. 24, 2019, which is herein incorporated by reference.

TECHNICAL FIELD

The present disclosure relates generally to three-dimensional digital scanners, and more particularly to intraoral three-dimensional digital scanners.

BACKGROUND

Dental impressions of a subject's intraoral three-dimensional surface, e.g., teeth and gingiva, are used for planning dental procedures. Traditional dental impressions are made using a dental impression tray filled with an impression material, e.g., PVS or alginate, into which the subject bites. The impression material then solidifies into a negative imprint of the teeth and gingiva, from which a three-dimensional model of the teeth and gingiva can be formed.

Digital dental impressions utilize intraoral scanning to generate three-dimensional digital models of an intraoral three-dimensional surface of a subject. Typically, a digital intraoral scanner has a window through which light enters and exits the scanner. For hygienic reasons, some intraoral scanners may utilize disposable sleeves that cover the portion of the scanner that is to be placed in a subject's mouth.

SUMMARY OF THE DISCLOSURE

An intraoral scanner is provided having an elongate handheld wand, a probe at a distal end of the wand, one or more light projectors, e.g., structured light projectors coupled to the handheld wand, and one or more cameras coupled to the handheld wand. Typically, a lower surface of the probe is a transparent surface, e.g., a window, through which light exits and enters the probe. Additionally, a transparent surface that is not integral to the probe, e.g., a window of a sleeve that is couplable to the probe, may be provided, such that, when coupled to the probe, the transparent surface and the window of the probe align with one another and light exits and enters the probe through the transparent surface as well as through the window of the probe.

In accordance with some applications of the present disclosure, a fluorescent transparent film is deposited either on the window of the probe or the transparent surface that is not integral to the probe. The one or more structured light projectors emit light and the one or more cameras acquire images of the object being captured, e.g., images of the intraoral scene. The projected light also stimulates the fluorescent transparent film to emit photons of a longer wavelength than the wavelength of the projected light. The photons emitted by the fluorescent transparent film are emitted in all directions. Thus, some of the emitted light from the fluorescent transparent film scatters backwards towards the one or more cameras and is captured by the one or more cameras. Color sensors in the one or more cameras may be used to differentiate between the light reflected by the fluorescent film and the light returning from the object being scanned.

For some applications, instead of a fluorescent transparent film being deposited on the window or the transparent surface, the window or the transparent surface itself, e.g., the window of the probe, or the window of a sleeve couplable to the probe, may be a window made of a fluorescent material.

There is therefore provided, in accordance with some applications of the present disclosure, an apparatus for intraoral scanning, the apparatus including:
- an elongate handheld wand including a probe at a distal end of the handheld wand;
- one or more light projectors coupled to the handheld wand;
- one or more cameras coupled to the handheld wand, each camera (a) including a camera sensor and objective optics including one or more lenses, and (b) configured to focus at an object focal plane that is located between 1 mm and 30 mm from the lens that is farthest from the camera sensor; and
- a fluorescent transparent film deposited on a surface selected from the group consisting of: a window of the probe through which light exits and enters the probe, and a transparent surface that is not integral to the probe.

For some applications, the one or more light projectors include one or more structured light projectors.

For some applications, the fluorescent transparent film includes a layer of fluorescent ink deposited on the selected surface.

For some applications, the fluorescent transparent film includes a layer of fluorescent polymer glued onto the selected surface.

For some applications, the layer of fluorescent polymer includes a fluorescent polymer tape.

For some applications, each structured light projector includes:
(a) at least one laser diode;
(b) a beam shaping optical element; and
(c) a pattern generating optical element configured to generate a distribution of discrete unconnected spots of light at all planes located between 1 mm and 30 mm from the pattern generating optical element when the laser diode is activated to transmit light through the pattern generating optical element.

For some applications, the apparatus further includes a processor configured to identify fluorescence of the fluorescent transparent film in an image captured by at least one of the cameras.

For some applications, the selected surface is the transparent surface that is not integral to the probe.

For some applications, the processor is configured to determine whether the transparent surface is present by identifying fluorescence of the fluorescent transparent film.

For some applications, the processor is configured to set a focal depth of the one or more cameras in response to identified presence of the transparent surface.

For some applications, the transparent surface includes a sleeve shaped and sized to be placed over the probe.

For some applications, the sleeve is rotationally asymmetric, and the rotational asymmetry of the sleeve is such as to assist the sleeve in correctly being placed over the probe such that the transparent surface is aligned with the window of the probe.

For some applications, the probe and a distal end of the sleeve have the same shape.

For some applications, the fluorescent transparent film includes a fluorescent barcode disposed on the transparent surface, and the processor is configured to identify the transparent surface by identifying the fluorescence of the fluorescent barcode.

For some applications, the processor is configured to identify that the transparent surface has previously been used by identifying that the fluorescent barcode has previously been identified by the processor.

For some applications, the fluorescent transparent film is shaped to provide a fluorescent identifier disposed on the transparent surface, and the processor is configured to identify the transparent surface by identifying the fluorescence of the fluorescent identifier.

For some applications, the processor is configured to identify that the transparent surface has previously been used, by identifying that the fluorescent identifier has previously been identified by the processor.

There is further provided, in accordance with some applications of the present disclosure, an apparatus for intraoral scanning, the apparatus including:

an elongate handheld wand including a probe at a distal end of the handheld wand;
one or more light projectors coupled to the handheld wand;
one or more cameras coupled to the handheld wand, each camera (a) including a camera sensor and objective optics comprising one or more lenses, and (b) configured to focus at an object focal plane that is located between 1 mm and 30 mm from the lens that is farthest from the camera sensor; and
a transparent window made of a fluorescent material, the transparent window selected from the group consisting of: a window of the probe through which light exits and enters the probe, and a window that is not integral to the probe.

For some applications, the one or more light projectors include one or more structured light projectors.

For some applications, the selected surface includes a fluorescent glass filter.

For some applications, the apparatus further includes a processor configured to identify fluorescence of the fluorescent material in an image captured by at least one of the cameras.

For some applications, the selected window is the window that is not integral to the probe.

For some applications, the apparatus further includes a sleeve shaped and sized to be placed over the probe, and wherein the window is disposed in a wall of the sleeve.

For some applications, the processor is configured to determine whether the window is present by identifying fluorescence of the window.

For some applications, the processor is configured to set a focal depth of the one or more cameras in response to identified presence of the window.

There is further provided, in accordance with some applications of the present disclosure, an apparatus for use with an elongate handheld wand of an intraoral scanner, the apparatus including:

a sleeve shaped and sized to be placed over a probe of the handheld wand, the sleeve including:
a window through which light enters and exits the probe when the sleeve is coupled to the probe, and
a fluorescent transparent film deposited on the window.

For some applications, the fluorescent transparent film includes a layer of fluorescent ink deposited on the window.

For some applications, the fluorescent transparent film includes a layer of fluorescent polymer glued onto the window.

For some applications, the layer of fluorescent polymer includes a fluorescent polymer tape.

For some applications, the fluorescent transparent film includes a fluorescent barcode disposed on the window.

For some applications, the fluorescent transparent film is shaped to provide a fluorescent identifier disposed on the window.

For some applications, the sleeve is rotationally asymmetric and the rotational asymmetry of the sleeve is such as to assist the sleeve in correctly being placed over the probe.

For some applications, the probe and a distal end of the sleeve have the same shape.

The present disclosure will be more fully understood from the following detailed description of applications thereof, taken together with the drawings, in which:

DETAILED DESCRIPTION

Figure 1:
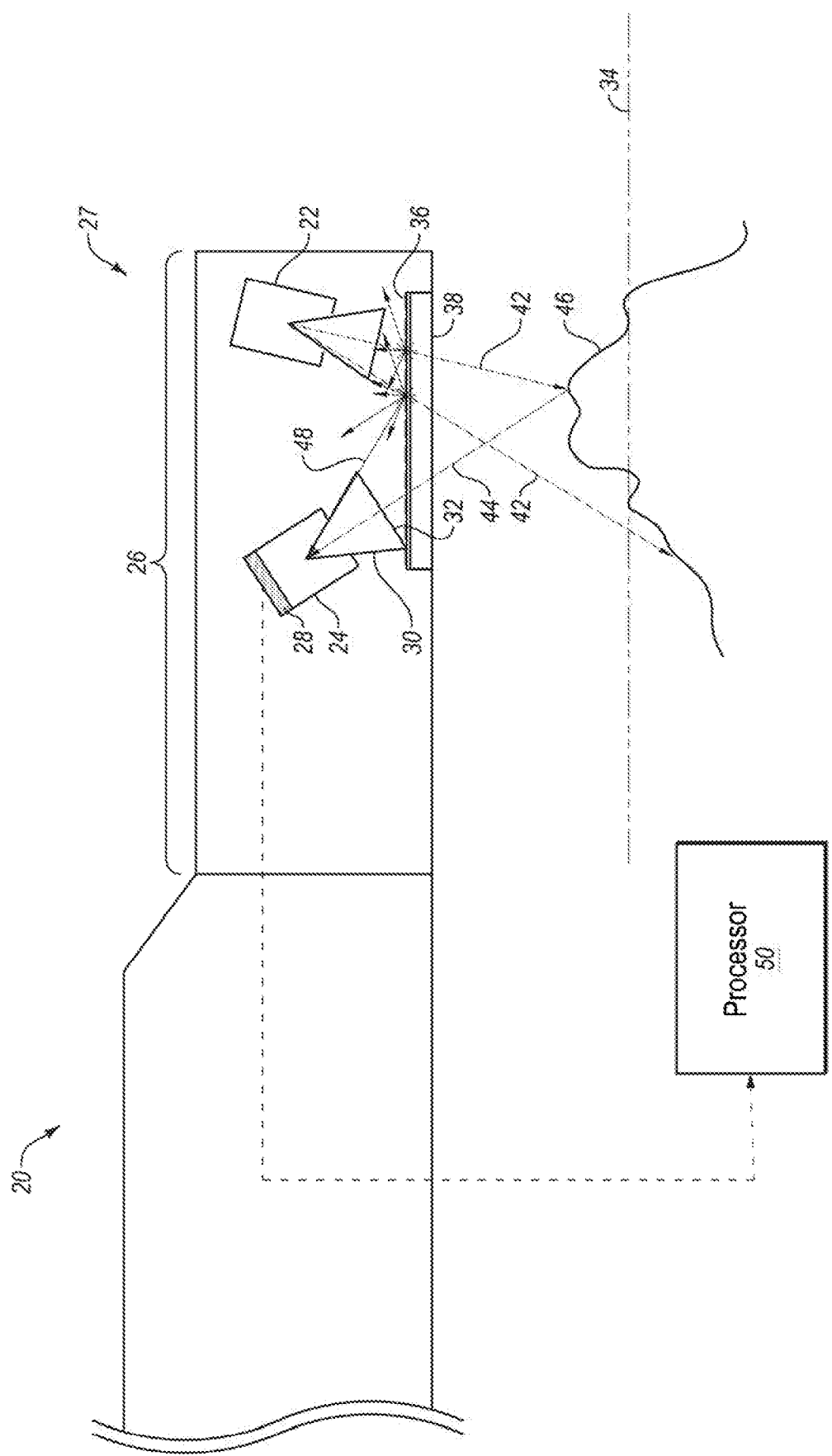
FIG. 1 is a schematic illustration of an elongate handheld wand with a structured light projector and a camera disposed within a probe at a distal end of the handheld wand, in accordance with some applications of the present disclosure.

Described herein are systems and techniques for optically detecting a window of an intraoral scanner and/or the presence of a sleeve on an intraoral scanner. An intraoral scanner may include a probe with a window through which incident light exits the probe and through which reflected light enters the probe. In embodiments, the intraoral scanner detects the presence of the window and/or the distance of the window from a lens (e.g., from a lens that is farthest from a sensor) and/or camera of the intraoral scanner using internal optics of the intraoral scanner and signal processing of a detected optical signal. At least a portion of the probe may be inserted into a sleeve, which may protect the probe and a patient from contact between the probe and the patient's oral cavity. The sleeve may include a window through which incident light exits the sleeve and through which reflected light enters the sleeve. In embodiments, the intraoral scanner detects the presence of the sleeve and/or the distance of a window of the sleeve from a lens or camera (e.g., from a lens that is farthest from a sensor of the intraoral scanner) using internal optics of the intraoral scanner and signal processing of a detected optical signal. For example, a portion of the incident light output by the probe may reflect off of the window of the sleeve, and the light reflected off of the window of the sleeve may be processed using one or more signal processing algorithms to detect the sleeve's window and thus the presence of the sleeve. Additionally or alternatively, the sleeve (e.g., a window of the sleeve) may emit light that is captured by a sensor of the intraoral scanner and processed using image processing or signal processing algorithms to detect the presence of the sleeve. Accordingly, internal optics of the intraoral scanner and image processing algorithms may be used to detect the presence or absence of a sleeve on the probe of the intraoral scanner. Additionally, in at least one embodiment the internal optics and image processing algorithms are used to determine a unique identifier (ID) of a sleeve on the probe. In at least one embodiment, at least a portion of the sleeve's window is coated with or otherwise includes a fluorescent material (e.g., a fluorescent film). Light generated by the intraoral scanner may cause the fluorescent material to fluoresce. The fluorescing material and thus the sleeve is then detected based on performing image processing or signal processing on light that has reflected off of the fluorescing material and/or light emitted by the fluorescing material on or in the sleeve's window.

In one embodiment, an intraoral scanner or computing device in communication with an intraoral scanner uses image data to detect the presence or absence of a sleeve on the intraoral scanner. In one embodiment, the intraoral scanner generates image data, processes the image data, and determines whether a sleeve is present or absent (e.g., whether or not a sleeve is disposed on the intraoral scanner) based on a result of the processing. In one embodiment, the image data that is generated is associated with fluorescence of a window of the sleeve. In one embodiment, if the sleeve is not detected, the intraoral scanner or computing device outputs an indication that the sleeve is not present and/or that a sleeve should be placed on the intraoral scanner. For example, the intraoral scanner may output an audible, tactile and/or visual indication, such as by activating a light, outputting a sound and/or vibrating.

Reference is now made to FIG. 1, which is a schematic illustration of an elongate handheld wand 20 with a light projector 22, e.g., a structured light projector 22, and a camera 24 disposed within a probe 26 at a distal end 27 of handheld wand 20, in accordance with some applications of the present disclosure. It is noted that FIG. 1 shows only one projector 22 and only one camera 24 by way of example and not limitation. For some applications, one or more structured light projectors 22 and one or more cameras 24 may be disposed within probe 26. Each of the one or more cameras 24 typically (a) has a camera sensor 28 and objective optics 30 comprising one or more lenses 32, and (b) focuses at an object focal plane 34 that is located at least 1 mm and/or less than 30 mm from the lens that is farthest from camera sensor 28. In some embodiments, elongate handheld wand 20 further includes one or more additional light sources (not shown) that may not generate structured light. The one or more additional light sources may be coherent or non-coherent light sources. In one embodiment, the one or more additional light sources are light emitting diodes. The one or more additional light sources may be activated at different times than the structured light projector 22 in embodiments. For example, the one or more additional light sources may be activated when elongate handheld want 20 is first turned an and/or at the beginning of the scanning procedure before scans are generated, and the one or more structured light projectors 22 may be activated when scans are to be generated.

Figure 2:
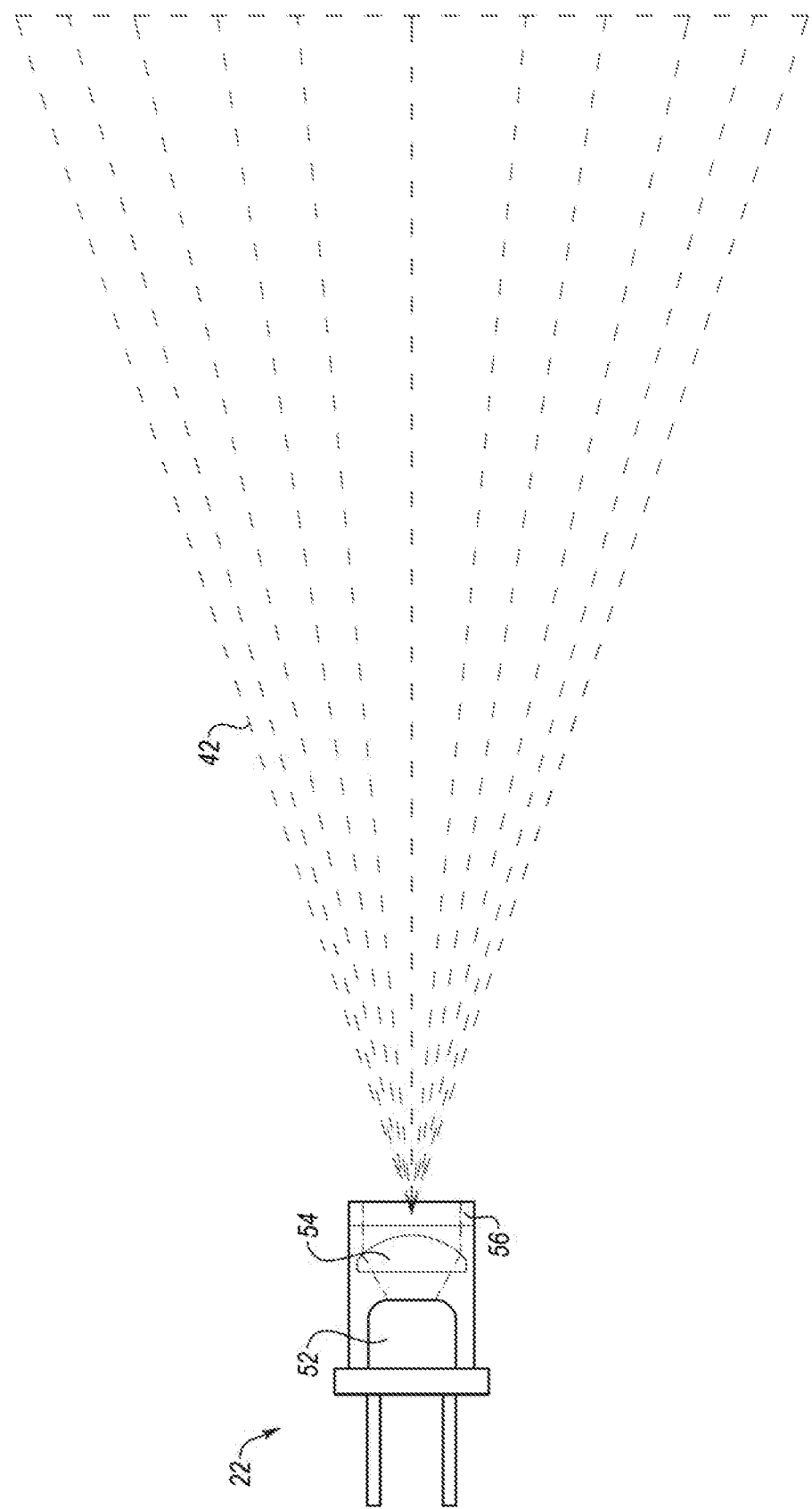
FIG. 2 is a schematic illustration of the structured light projector, in accordance with some applications of the present disclosure.

Reference is now made to FIG. 2, which is a schematic illustration of structured light projector 22, in accordance with some applications of the present disclosure. Typically, each structured light projector 22 comprises (a) at least one laser diode 52, (b) a beam shaping optical element 54, and (c) a pattern generating optical element 56, which generates a distribution of discrete unconnected spots of light at all planes, e.g., object focal plane 34, located at least 1 mm and/or less than 30 mm from pattern generating optical element 56 when laser diode 52 is activated to transmit light through pattern generating optical element 56.

Reference is again made to FIG. 1. Typically, a lower surface of probe 26 is a transparent surface, e.g., a window 38, through which light exits and enters probe 26. Additionally, a transparent surface 40 that is not integral to probe 26, e.g., a window of a sleeve that is couplable to probe 26, may be provided, further described hereinbelow with reference to FIGS. 3A-C. The window of the sleeve and/or window 38 of the probe may be composed of any suitable transparent material, such as glass, plastic, quartz, and/or other material. When coupled to probe 26, transparent surface 40 and window 38 of probe 26 align with one another such that light exits and enters probe 26 through transparent surface 40 that is not integral to probe 26 as well as through window 38 of probe 26.

In accordance with some applications of the present disclosure, a fluorescent transparent film 36 is deposited either on window 38 of probe 26 or on transparent surface 40. Arrows 42 schematically represent light projected by one or more structured light projectors 22. Arrow 44 schematically represents the projected light reflecting off of an object 46, e.g., intraoral surface, being scanned, e.g., a three-dimensional intraoral surface, and entering one or more cameras 24, such that one or more cameras 24 acquire images of the object being scanned, e.g., of the intraoral scene. In some embodiments, the light projected by one or more structured light projectors 22 also stimulates fluorescent transparent film 36 to emit photons of a longer wavelength than the wavelength of the projected light. Typically, fluorescent transparent film 36 is tuned to emit photons of a predetermined wavelength, e.g., at least 520 nm and/or less than 680 nm, or at least 410 nm and/or less than 700 nm, or within the visible spectrum of light. This is based on a phenomenon known as Stokes shift, whereby the illumination photons are absorbed by the molecules in the fluorescent layer, which then enter an excited state. As the excited molecules relax, they emit photons which have less energy than the absorbed photons, resulting in an emission of photons of longer wavelength than the illumination photons. The optical system of handheld wand 20 may include one or more filters and/or other optical components, which may filter out one or more wavelengths of light. The selection of such filters in the optical system may be influenced by the wavelengths of light that excite fluorescent layer and/or by the wavelengths of light emitted by fluorescent layer. In embodiments, fluorescent material choice influences optical part selection for the handheld wand.

The fluorescent layer, filters and/or light sources (e.g., structured light projectors and/or additional light sources) may be selected to work together. For example, if the structured light projectors are to excite the fluorescent layer, then the structured light projectors and fluorescent layer may be selected such that wavelengths output by the structured light projectors output light that causes the fluorescent material to fluoresce. If the one or more additional light projectors are to excite the fluorescent layer, then the structured light projectors and fluorescent layer may be selected such that the light output by the structured light projectors does not cause the fluorescent layer to fluoresce, and the one or more additional light sources may be selected such that a wavelength of light output by the one or more additional light projectors does cause the fluorescent layer to fluoresce. Additionally, the filters may be selected such that they do not filter out wavelengths of light that cause the fluorescent filter to fluoresce and/or wavelengths of light emitted by the fluorescent layer.

Fluorescent transparent film 36 may be tuned to emit photons of a predetermined wavelength, e.g., at least 520 nm and/or less than 680 nm, or at least 410 nm and/or less than 700 nm, or within the visible spectrum of light. Some examples of fluorescent material that may be used for the fluorescent layer include Alexa Fluor® 405, which has a maximum absorbance of around 401 nm and a maximum emission of around 421 nm, Alexa Fluor® 488, which has a maximum absorbance of around 495 nm and a maximum emission of around 519 nm, Alexa Fluor® 647, which has a maximum absorbance of around 650 nm and a maximum emission of around 665 nm, Alexa Fluor® 700, which has a maximum absorbance of around 702 nm and a maximum emission of around 723 nm, APC, which has a maximum absorbance of around 650 nm and a maximum emission of around 661 nm, Cy5, which has a maximum absorbance of around 649 nm and a maximum emission of around 670 nm, DyLight® 405, which has a maximum absorbance of around 400 nm and a maximum emission of around 420 nm, DyLight® 488, which has a maximum absorbance of around 493 nm and a maximum emission of around 518 nm, DyLight® 549, which has a maximum absorbance of around 562 nm and a maximum emission of around 576 nm, DyLight® 649, which has a maximum absorbance of around 654 nm and a maximum emission of around 673 nm, DyLight® 680, which has a maximum absorbance of around 692 nm and a maximum emission of around 712 nm, DyLight® 750, which has a maximum absorbance of around 752 nm and a maximum emission of around 778 nm, DyLight® 800, which has a maximum absorbance of around 777 nm and a maximum emission of around 794 nm, FITC, which has a maximum absorbance of around 490 nm and a maximum emission of around 525 nm, Pacific Blue™, which has a maximum absorbance of around 410 nm and a maximum emission of around 455 nm, PerCP, which has a maximum absorbance of around 490 nm and a maximum emission of around 675 nm, PE, which has a maximum absorbance of around 490 or 565 nm and a maximum emission of around 578 nm, Texas Red®, which has a maximum absorbance of around 596 nm and a maximum emission of around 615 nm, and TRITC, which has a maximum absorbance of around 596 nm and a maximum emission of around 570 nm. These are merely examples of fluorescent materials, and any other types of fluorescent materials may also be used.

In some embodiments, elongate handheld wand 20 further includes the one or more additional light sources mentioned above, and the one or more additional light sources emit light that causes the fluorescent transparent film 36 to fluoresce and therefore to emit photons of the longer wavelength than the wavelength of the projected light being absorbed by the fluorescent transparent film 36.

For some applications fluorescent transparent film 36 is a layer of fluorescent ink, e.g., a fluorescent material mixed in a polymeric solution, deposited on window 38 of probe 26, or on transparent surface 40. Alternatively, for some applications fluorescent transparent film 36 may be a layer of fluorescent polymer glued onto window 38 of probe 26 or onto transparent surface 40. For some applications, the fluorescent polymer may be a fluorescent polymer tape. In some embodiments, the window 38 of probe 26 and/or transparent surface 40 is doped with a fluorescent material instead of or in addition to there being a fluorescent layer or film disposed on the transparent surface 40 and/or window 38.

In some embodiments, some of the emitted light 48 from the fluorescent transparent film scatters backwards towards the one or more cameras 24 and is captured by camera sensor 28 along with the structured light from one or more structured light projectors 22 reflecting off the object being scanned. In some embodiments, in which the one or more additional light sources were used to excite the fluorescent transparent film, some of the emitted light 48 from the fluorescent transparent film scatters backwards towards the one or more cameras 24 and is captured by camera sensor 28, possibly along with the unstructured light from the one or more additional light sources reflecting off an object and/or off of the window or transparent surface 40. For some applications, structured light projector 22 and/or the one or more additional light sources projects light of a specific wavelength, and fluorescent transparent film 36 is tuned to emit light at a wavelength of a different wavelength than projected light 42. Camera sensor 28, which is typically, but not necessarily, a color sensor, captures (a) reflected light 44 reflecting off the object being scanned and (b) emitted light 48 from fluorescent transparent film 36. A processor 50 is used to process the captured images and to identify fluorescence of fluorescent transparent film 36 in an image captured by at least one of one or more cameras 24, by differentiating between emitted light 48 emitted by transparent fluorescent film 36 and the returned optical image from reflected light 44, which may be light returning from object 46 being scanned, based on color in the captured image.

For some applications, processor 50 may run a 3-dimensional image reconstruction algorithm based on structured projected light 42 and reflected light 44 returning from object 46 being scanned. Emitted light 48 emitted by transparent fluorescent film 36, differing in color from reflected light 44, as described hereinabove, allows processor 50 to easily exclude emitted light 48 from the 3-dimensional image reconstruction algorithm. If the one or more additional light sources are used to emit light that excites the fluorescent film, then the light projected by structured light projectors 22 may have a wavelength that does not cause the fluorescent film to fluoresce (e.g., does not excite the fluorescent film).

For some applications, at least one or more projectors 22 may project broadband light onto object 46 being scanned, in order for cameras 24 to capture a 2-dimensional color-image of object 46. In this case, the wavelength of emitted light 48 emitted by transparent fluorescent film 36 may be the same, or similar, as a wavelength in the captured color-image. The inventors have realized two ways of ensuring that processor 50 can differentiate between emitted light 48 and the returned optical image. The first is to capture the 2-dimensional color-image using broadband light that is shifted towards the short-wavelength end of the color spectrum, e.g., toward the violet end of the spectrum, such that emitted light 48 emitted by transparent fluorescent film 36 has a longer wavelength than any of the wavelengths in the shifted broadband light. Processor 50 can thus identify the fluorescence based on color, as described hereinabove. Alternatively or additionally, transparent fluorescent film 36 may be shaped to define a distinct form that is not generally found in nature, e.g., a distinct shape, a series of letters or digits, a barcode, or a unique identifier. Thus, even if the wavelength of emitted light 48 is the same, or similar, as a wavelength in the color image, emitted light 48 will have a distinct form in the color-image and can thus be identified by processor 50. Alternatively, or additionally, if the one or more additional light projectors are used to excite the fluorescent film, then the fluorescent film may be selected such that it does not fluoresce based on any of the wavelengths of light in the broadband light output by the at least one or more projectors 22.

In one embodiment, elongate handheld wand 20 may alternate between powering on structured light projectors 22 and/or the one or more additional light projectors. In some embodiments, the one or more additional light source is powered on at a beginning of scanning, such as when elongate handheld wand 20 is activated, to detect the presence or absence of a sleeve thereon. During scanning, elongate handheld wand 20 may alternate between use of structured light projectors 22 and one or more additional light sources. Structured light emitted by the structured light projector 22 passes through window and the fluorescent film without causing the fluorescent film to fluoresce. Thus, the fluorescent film does not negatively impact an ability of elongate handheld wand 20 to accurately scan intraoral objects. Light emitted by the one or more additional light sources, on the other hand, cause fluorescent film to fluoresce and emit light.

Figure 3A:
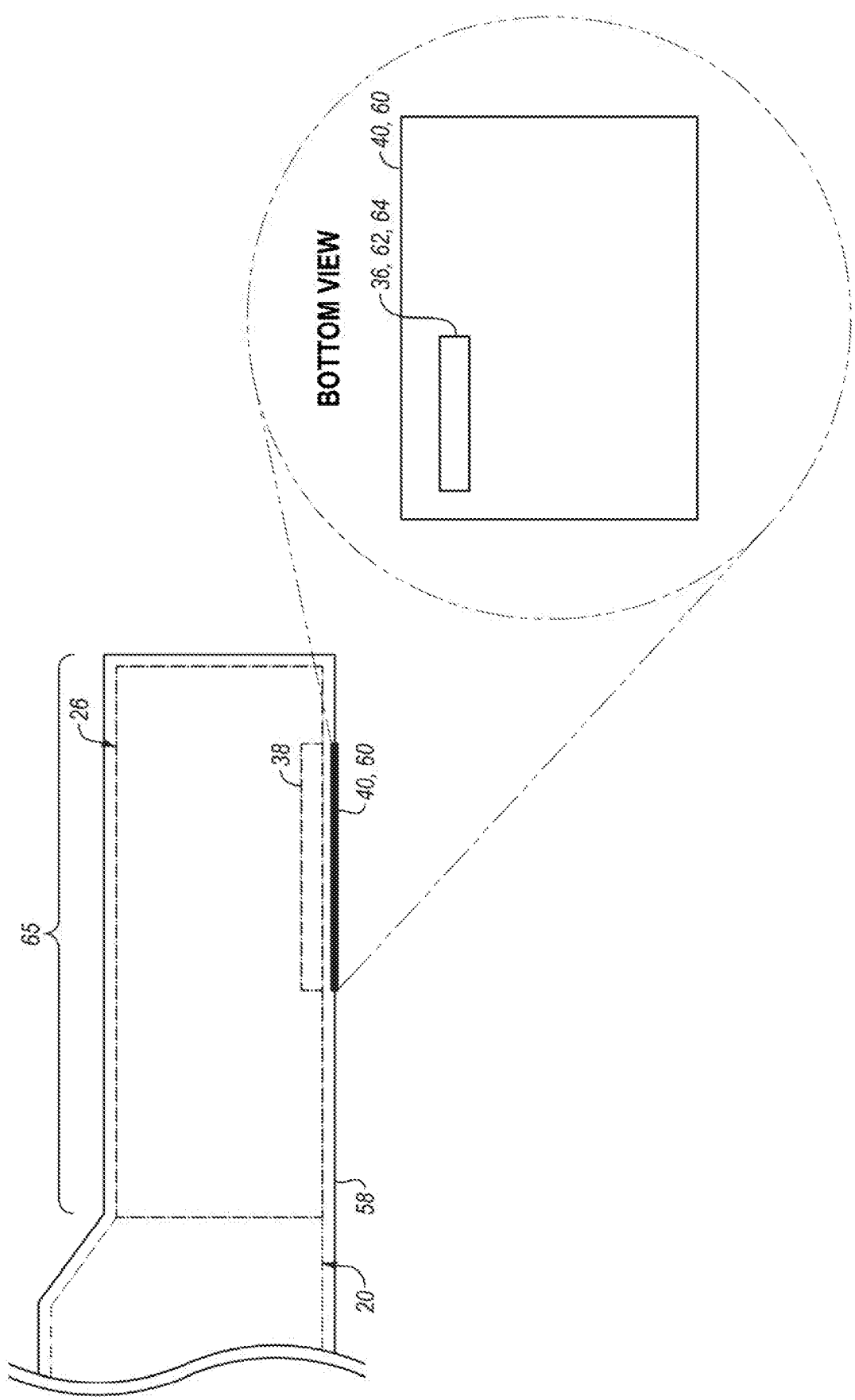
FIG. 3A is a schematic illustration of a sleeve that is couplable to the probe in accordance with some applications of the present disclosure.

Reference is now made to FIG. 3A, which is a schematic illustration of a sleeve 58 that is couplable to probe 26 in accordance with some applications of the present disclosure. For some applications, sleeve 58 is sized and shaped to be placed over probe 26 of handheld wand 20. Typically, sleeve 58 is rotationally asymmetrical, which assists a practitioner to correctly place sleeve 58 over probe 26 such that transparent surface 40, e.g., a window 60 of sleeve 58, is aligned with window 38 of probe 26. Typically, but not necessarily, probe 26 and a distal end 65 of sleeve 58 have the same shape.

As described hereinabove, transparent surface 40 that is not integral to probe 26 may be window 60 of sleeve 58, through which light enters and exits probe 26 when sleeve 58 is coupled to probe 26. Fluorescent transparent film 36 may be deposited on window 60. Fluorescent transparent film 36 deposited on window 60 may be any of the options listed hereinabove with reference to FIG. 1, e.g., a layer of fluorescent ink, a layer of fluorescent polymer, or a fluorescent polymer tape. Alternatively, or additionally, window 60 may be doped with a fluorescent dopant rather than or in addition to having a fluorescent film disposed thereon.

It is noted that handheld wand 20, including probe 26, is shown in FIG. 3A in order to illustrate how sleeve 58 is coupled to probe 26. As such, handheld wand 20, including probe 26, is shown in dashed lines in FIG. 3, and projector(s) 22, camera(s) 24, and processor 50 are not shown in FIG. 3A.

Figure 3C:
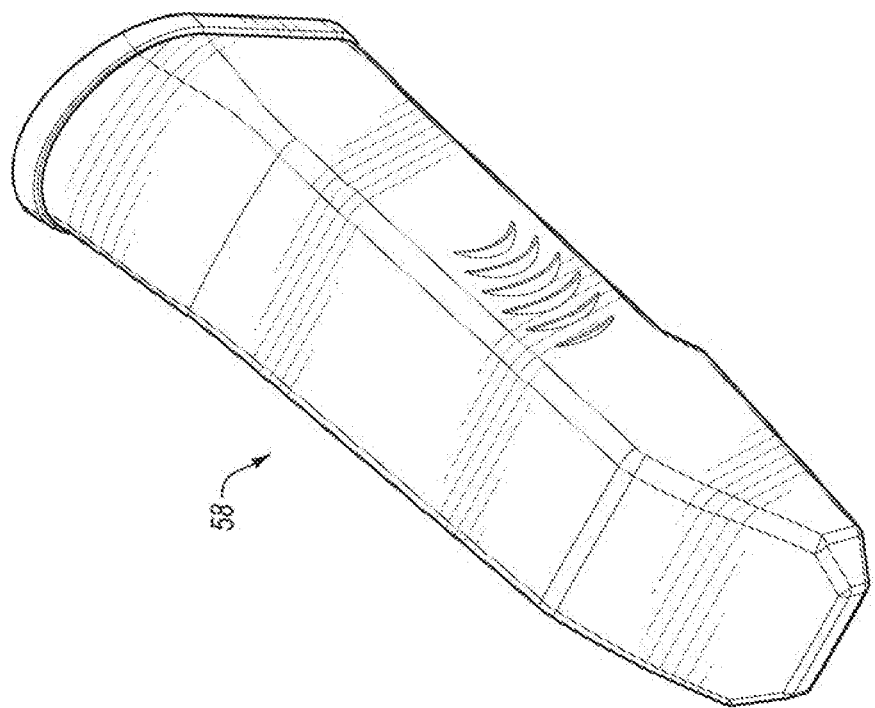
FIGS. 3B-C are isometric views of the sleeve of FIG. 3A, in accordance with some applications of the present disclosure.
Figure 3B:
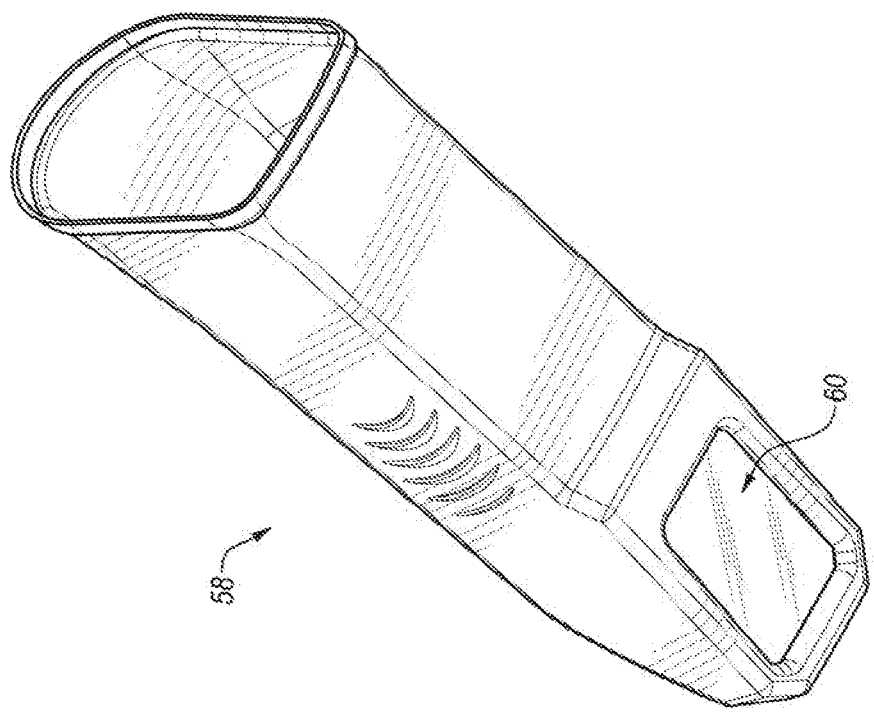

Reference is now made to FIGS. 3B-C, which are isometric views of sleeve 58, in accordance with some applications of the present disclosure. In FIG. 3B, for illustrative purposes the sleeve is shown in the opposite orientation to FIG. 3A, such that window 60 is visible from above. FIG. 3C shows the same sleeve 58 as in FIG. 3B, but flipped such that window 60 is not visible from above.

As described hereinabove, processor 50 is used to process the captured images and to identify fluorescence of fluorescent transparent film 36 in an image captured by at least one of one or more cameras 24. For some applications, when fluorescent transparent film 36 is deposited on transparent surface 40, e.g., window 60 of sleeve 58, processor 50 may be used to determine whether transparent surface 40, e.g., window 60, is present by identifying fluorescence of fluorescent transparent film 36. Due to hygienic reasons it may be undesirable for the probe 26 to be placed into the mouth of a subject without the presence of sleeve 58. Thus, for some applications, if the intraoral scanner is activated and processor 50 does not identify the presence of sleeve 58, the practitioner may be alerted to place a sleeve 58 on probe 26 prior to placement of probe 26 in the subject's mouth. For example, a visual alert may appear on a display screen associated with the intraoral scanner, or an audio alert may sound.

For some applications, it may be desirable to not only determine the presence of a sleeve 58, but to also identify a specific sleeve 58. Due to hygienic reasons it may be undesirable to use the same sleeve for more than one patient. Additionally, or alternatively, for commercial reasons it may be desirable to identify if a sleeve 58 is from a specific manufacturer for sleeve authentication. Thus, it is useful for processor 50 to identify a specific sleeve 58, and to further identify whether specific sleeve 58 has been used by identifying whether the specific sleeve 58 has previously been identified by processor 50. For some applications, fluorescent transparent film 36 may be a fluorescent barcode 62 or may be shaped to provide a fluorescent identifier 62 disposed on transparent surface 40, e.g., on window 60 of sleeve 58, that is unique to each sleeve 58. Processor 50 thus identifies transparent surface 40, e.g., window 60 of sleeve 58, by identifying the fluorescence of fluorescent barcode 62 or fluorescent identifier 64. Processor 50 may identify that a specific sleeve 58 has previously been used by identifying that fluorescent barcode 62 or fluorescent identifier 64 has previously been identified by processor 50.

For some applications fluorescent barcode 62 may include a 1-dimensional barcode, e.g., a Universal Product Code (UPC), which is typically a string of vertical bars that vary in thickness, or a 2-dimensional barcode, e.g., a Quick Response (QR) Code, a Data Matrix code, a PDF417 code, or an AZTEC code. For some applications, fluorescent identifier 64 may be an identifying code, such as a unique string of digits and/or letters and/or graphical representations.

For some applications, it may be desirable for processor 50 to determine a position of sleeve 58 with respect to one or more cameras 24 when sleeve 58 is coupled to probe 26, e.g., the distance between one or more cameras 24 and window 60. Processor 50 is able to determine the position of sleeve 58 by identifying fluorescence of fluorescent transparent film 36 on transparent surface 40, e.g., on window 60 of sleeve 58. One or more cameras 24 may have a variety of possible focal depths, and processor 50 may set a specific focal depth of one or more cameras 24 in response to the identified position of external transparent surface 40, e.g., window 60 of sleeve 58. For some applications, the intraoral scanner may utilize confocal scanning to perform 3-dimensional imaging in a patient's mouth. In response to the determination of the position of sleeve 58 with respect to one or more cameras 24, processor 50 may set the position of window 60 as the zero-position on the z-axis used for confocal depth scanning. This allows the cameras to ignore saliva that may be present on window 60.

For some applications, fluorescent transparent film 36 may be positioned on window 60 such that processor 50 can identify if window 60 of sleeve 58 is aligned with window 38 of probe 26, in response to identifying fluorescence of fluorescent transparent film 36.

For some applications, alternatively to a fluorescent transparent film being deposited on either window 38 of probe 26 or on transparent surface 40 that is not integral to probe 26

(e.g., on window 60 of sleeve 58), the window itself may be made of a fluorescent material, e.g., a fluorescent glass filter. An example of a fluorescent glass filter is Edmund Optics Lumilass Fluorescent Glass Filters. In contrast to processor 50 identifying fluorescence of a transparent fluorescent film, in this case, processor 50 identifies fluorescence of the fluorescent material. Processor 50 may identify the presence of sleeve 58 in response to identifying fluorescence of the fluorescent material in an image captured by at least one of the cameras 24.

Embodiments have been discussed with reference to systems and methods for detecting a probe window and/or a presence or absence of a sleeve for an intraoral scanner having one or more cameras and one or more light projectors at a distal end of a probe of the intraoral scanner. It should be understood that the embodiments discussed herein are also applicable to other intraoral scanner designs, such as those in which light projectors and/or image sensors such as cameras are not disposed in the distal end of the probe. For example, the embodiments described herein also apply to intraoral scanners in which light projectors and/or sensors or detectors are disposed at or near a proximal end of a probe of such intraoral scanners. Embodiments discussed herein apply, for example, to intraoral scanners that determine depth based on adjusting a focal setting of an optical system of the intraoral scanner and determining focal settings at which an image is determined to be clearest and/or to have a highest intensity, such as intraoral scanners with a confocal optics system.

Figure 4:
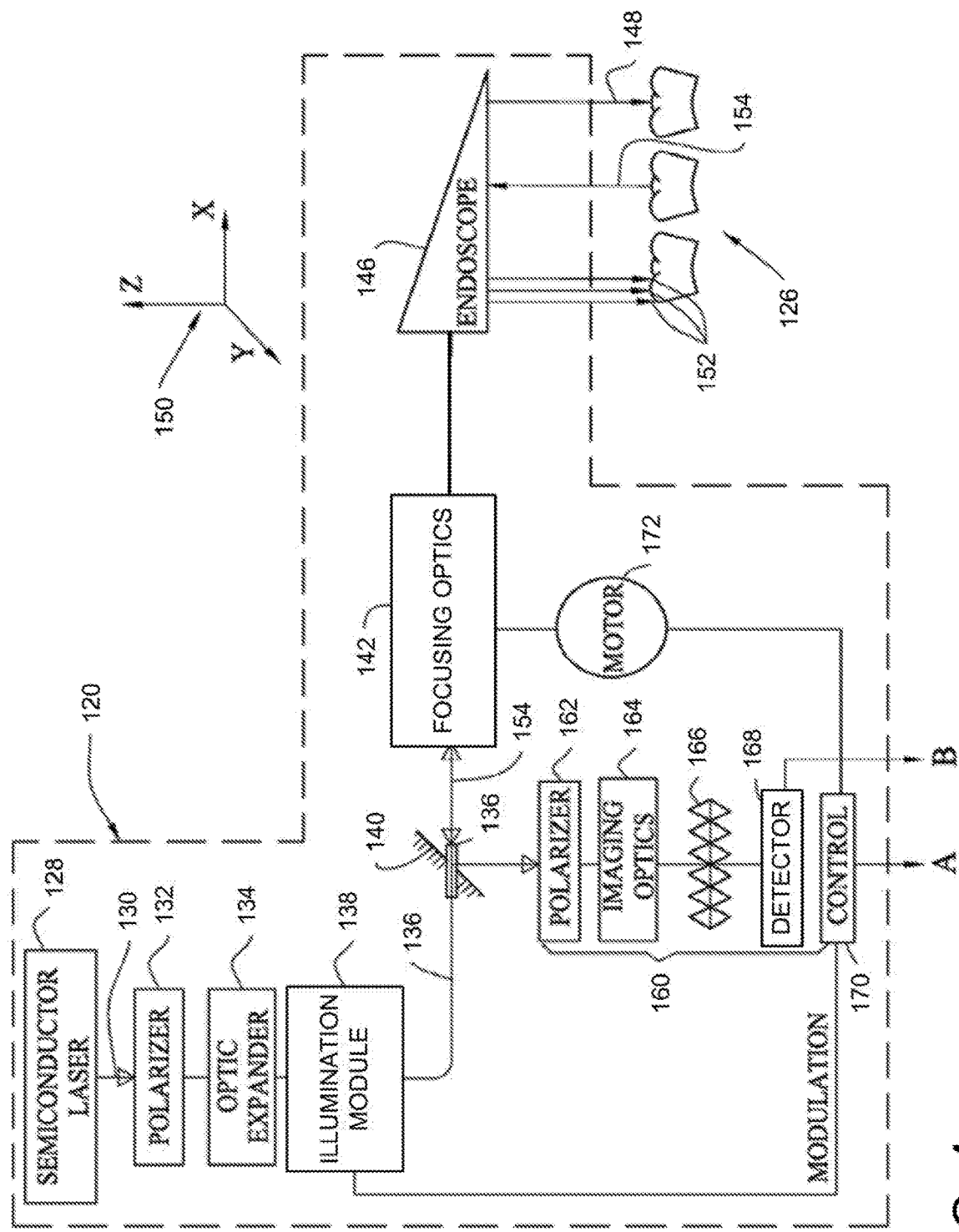
FIG. 4 illustrates an intraoral scanner 120, in accordance with embodiments of the present disclosure.

FIG. 4 illustrates an intraoral scanner 120, in accordance with embodiments of the present disclosure. In one embodiment, the techniques described herein are applied to an intraoral scanner that includes a semiconductor laser unit 128 or other light source that emits light such as a focused light beam, as represented by arrow 130. The light 130 passes through a polarizer 132. Polarizer 132 polarizes the light passing through polarizer 132. Alternatively, polarizer 132 may be omitted in some embodiments. The light then enters into an optic expander 134 that improves a numerical aperture of the light beam 130. In one embodiment, the light 130 passes through an illumination module 138, which splits the light 130 into an array of incident light beams, represented here, for ease of illustration, by a single line. Alternatively, or additionally, the illumination module 138 may impart some image pattern on the light. The illumination module 138 may be, for example, a grating or a micro lens array that splits the light 130 into an array of light beams. Alternatively, the illumination model may be a checkerboard pattern or other static or time varying pattern that causes light passing therethrough to have the pattern. Modified light 136 (e.g., patterned light and/or an array of light beams) is output by the illumination module 138.

The scanner 120 may further include a unidirectional mirror or beam splitter (e.g., a polarizing beam splitter) 40 that passes the modified light 136. A unidirectional mirror 140 allows transfer of light from the semiconductor laser 128 or other light source through to downstream optics, but reflects light travelling in the opposite direction. A polarizing beam splitter allows transfer of light having a particular polarization and reflects light having a different (e.g., opposite) polarization. In one embodiment, the unidirectional mirror or beam splitter 140 has a small central aperture. The small central aperture may improve a measurement accuracy of the scanner 120. In one embodiment, as a result of a structure of the unidirectional mirror or beam sputter 140, the modified light will yield a light annulus on an illuminated area of an imaged object as long as the area is not in focus. Moreover, the annulus will become a completely illuminated spot or point once in focus. This ensures that a difference between measured intensities of out-of focus points and in-focus points will be larger.

Along an optical path of the modified light after the unidirectional mirror or beam splitter 140 are focusing optics 142 (which may or may not be confocal imaging optics), and an endoscopic probing member 146. Additionally, a quarter wave plate may be disposed along the optical path after the unidirectional mirror or beam splitter 140 to introduce a certain polarization to the modified light. In some embodiments this may ensure that reflected light will not be passed through the unidirectional mirror or beam splitter 140. Focusing optics 142 may additionally include relay optics (not shown). Focusing optics 142 may or may not maintain the same magnification of an image over a wide range of distances in the 7 direction, wherein the 7 direction is a direction of beam propagation (e.g., the 7 direction corresponds to an imaging axis that is aligned with an optical path of the modified light 136). The relay optics enable the scanner 120 to maintain a certain numerical aperture for propagation of the modified light 136.

The endoscopic probing member 146 may include a rigid, light-transmitting medium, which may be a hollow object defining within it a light transmission path or an object made of a light transmitting material, e.g. a glass body or tube. In one embodiment, the endoscopic probing member 146 include a prism such as a folding prism. At its end, the endoscopic probing member 146 may include a mirror of the kind ensuring a total internal reflection. Thus, the mirror may direct the modified light towards a teeth segment 126 or other object. The endoscope probing member 146 thus emits modified light 148 (e.g., an array of light beams and/or patterned light), which impinge on to surfaces of the teeth section 126.

The modified light 148 may be arranged in an X-Y plane, in the Cartesian frame 150, propagating along the Z axis. As the surface on which the incident light hits is an uneven surface, illuminated points 152 are displaced from one another along the Z axis, at different $(X_i, Y_i)$ locations, Thus, while a point at one location may be in focus of the confocal focusing optics 142, points at other locations may be out-of-focus. Therefore, the light intensity of returned light of the focused points will be at its peak, while the light intensity at other points will be off peak. Thus, for each illuminated point or area, multiple measurements of light intensity are made at different positions along the Z-axis. For each of such $(X_i, Y_i)$ location, the derivative of the intensity over distance (Z) may be made, with the $Z_i$ yielding maximum derivative, $Z_0$, being the in-focus distance. In one embodiment, the incident light from an array of light beams forms a light disk on the surface when out of focus and a complete light spot when in focus, Thus, the distance derivative will be larger when approaching in-focus position, increasing accuracy of the measurement.

The light scattered from each of the light points may include a beam travelling initially in the Z axis along the opposite direction of the optical path traveled by the modified light 148. Returned light 154 is received by the endoscope 46 and directed back through focusing optics 142. In one embodiment, a returned light beam (e.g., which may be from an array of returning light beams) corresponds to one of an array of incident light beams, Given the asymmetrical properties of unidirectional mirror or beam splitter 140, the returned light is reflected in the direction of detection optics 160.

The detection optics 160 may include a polarizer 162 that has a plane of preferred polarization oriented normal to the plane polarization of polarizer 132. Alternatively, polarizer 132 and polarizer 162 may be omitted in some embodiments. The returned light 154 may pass through imaging optics 164 in one embodiment. The imaging optics 164 may be one or more lenses. Alternatively, the detection optics 160 may not include imaging optics 164. In one embodiment, the returned light 154 further passes through a matrix 166, which may be an array of pinholes. Alternatively, no matrix 166 is used in some embodiments. The returned light 154 is then directed onto a detector 168.

The detector 168 is an image sensor having a matrix of sensing elements each representing a pixel of the image or scan. If matrix 166 is used, then each pixel further corresponds to one pinhole of matrix 166. In one embodiment, the detector is a charge coupled device (CCD) sensor, in one embodiment, the detector is a complementary metal-oxide semiconductor (CMOS) type image sensor. Other types of image sensors may also be used for detector 168, The detector 168 detects light intensity and/or other light properties at each pixel.

In one embodiment, detector 168 provides data to computing device via signal B. Thus, each light intensity measured in each of the sensing elements of the detector 168, is then captured and analyzed.

Scanner 120 further includes a control module 170 connected both to semiconductor laser 128 or other light source and a motor 172, voice coil or other translation mechanism. In one embodiment, control module 170 is or includes a field programmable gate array (FPGA) configured to perform control operations. Motor 172 is linked to focusing optics 142 for changing a focusing setting of focusing optics 142. This may adjust the relative location of a focal surface of focusing optics 142 along the Z-axis (e.g., in the imaging axis). Control module 170 may induce motor 172 to axially displace (change a location of) one or more lenses of the focusing optics 142 to change the focal depth of the focal surface. In one embodiment, motor 172 or scanner 120 includes an encoder (not shown) that accurately measures a position of one or more lenses of the focusing optics 142. The encoder may include a sensor paired to a scale that encodes a linear position. The encoder may output a linear position of the one or more lenses of the confocal focusing optics 142. The encoder may be an optical encoder, a magnetic encoder, an inductive encoder, a capacitive encoder, an eddy current encoder, and so on, After receipt of feedback that the location of the one or more lenses has changed, control module 170 may induce laser 128 or other light source to generate a light pulse. Control unit 170 may additionally synchronize a computing device to receive and/or store data representative of the light intensity from each of the sensing elements at the particular location of the one or more lenses (and thus of the focal depth of the imaginary non-flat focal surface) via signal A and signal B. In subsequent sequences, the location of the one or more lenses (and thus the focal depth) will change in the same manner and the data capturing will continue over a wide focal range of focusing optics 142.

A computing device may capture images responsive to receiving image capture commands from the control unit 170. The captured images may be associated with a particular focusing setting (e.g., a particular location of one or more lenses in the focusing optics as output by the encoder). In one embodiment, the computing device then processes captured images or scans captured over multiple different focusing settings. The computing device may determine the relative intensity in each pixel over the entire range of focal settings of focusing optics 142 from received image data. Once a certain light point associated with a particular pixel is in focus, the measured intensity will be maximal for that pixel, Thus, by determining the $Z_i$ corresponding to the maximal light intensity or by determining the maximum displacement derivative of the light intensity, for each pixel, the relative position of each point of light along the Z axis can be determined for each pixel. Thus, data representative of the three-dimensional pattern of a surface in the teeth segment 26 or other three dimensional object can be obtained.

In at least some embodiments, scanner 120 includes a window through which light exits endoscope 146 and through which returning light enters endoscope 146. In embodiments, the window includes a fluorescent material therein or thereon. The fluorescent material may be, for example, a film coated on a portion of the window or on an entirety of the window, as discussed herein above. Semiconductor laser 128 or another light source of scanner 120 may cause the fluorescent material to fluoresce, and light output by the fluorescing material may be detected by detector 168. The detected light output by the fluorescing material may be used to detect the window and/or a state of the window.

In at least some embodiments, a protective sleeve (not shown) is disposed over a probe of the scanner 120 that includes the endoscope 146. The protective sleeve may include a window that may align with a window of the probe. The window of the protective sleeve may include a fluorescent material therein or thereon instead of or in addition to the window of the probe. The fluorescent material on the window of the protective sleeve may be excited by semiconductor laser 128 or another light source of scanner 120, and the light output by the fluorescening material may be detected by detector 168 and used to detect a presence of the protective sleeve and/or a state of the protective sleeve. In an example, the light emitted by the fluorescing material may be used to determine whether the protective sleeve is properly seated on the probe, such as by detecting a distance of one or more points of the window from the focusing optics and comparing the detected distance to a target distance. If the detected distance is different from the target distance, then a determination may be made that the protective sleeve is not properly placed on the probe of the intraoral scanner 120, for example.

Figure 5A:
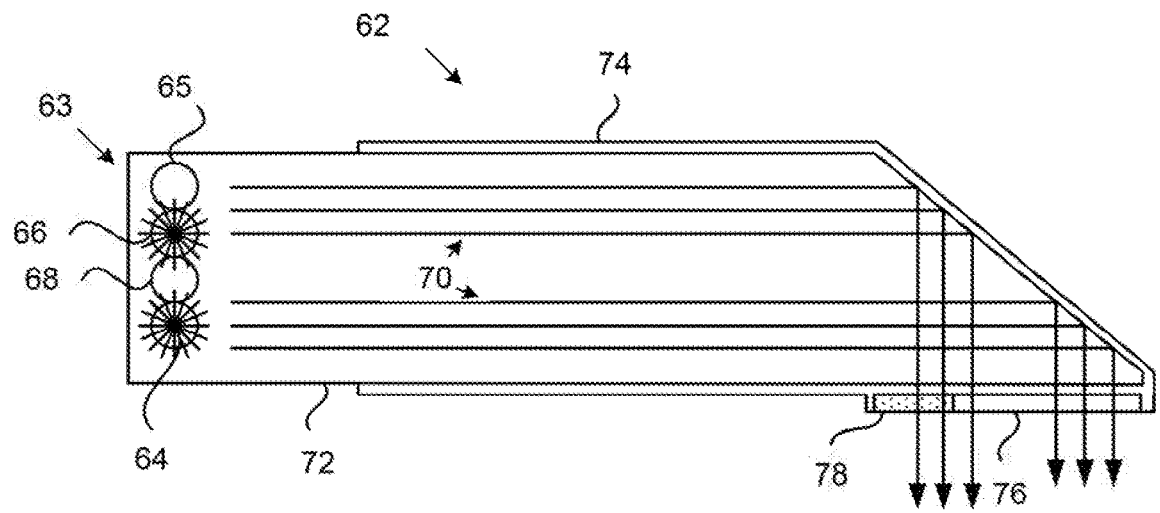
FIGS. 5A-5B illustrate operation of an intraoral scanner that includes light sources disposed elsewhere than a distal end of a probe of the intraoral scanner, and that further includes a protective sleeve having a window with a fluorescent material on or in at least a portion of the window, in accordance with embodiments of the present disclosure.
Figure 5B:
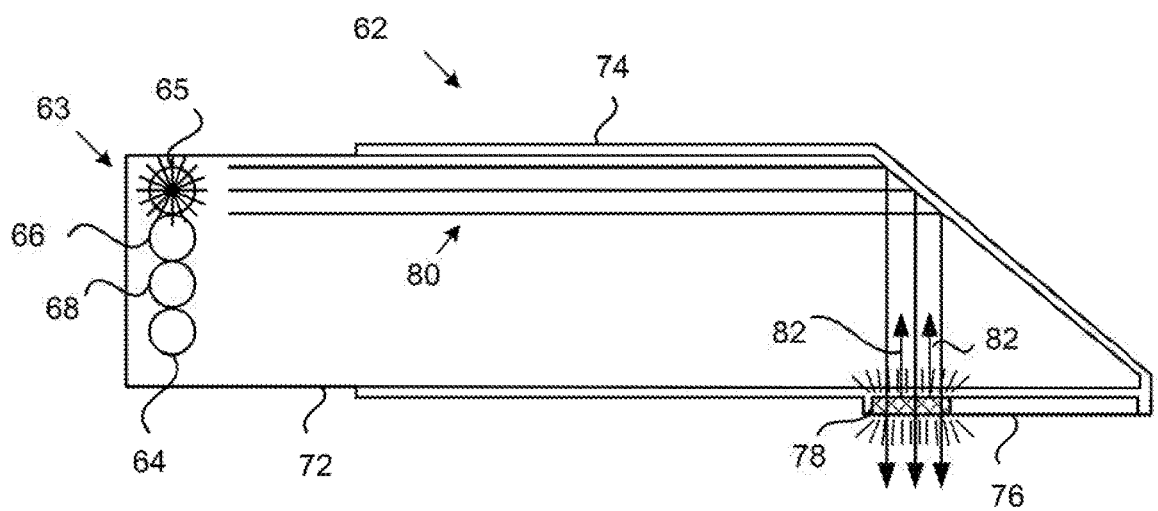

FIGS. 5A-5B illustrate operation of an intraoral scanner 62 that includes light sources disposed elsewhere than a distal end of a probe 72 of the intraoral scanner 62. As shown, probe 72 includes a protective sleeve 74 disposed thereon. Protective sleeve 74 includes a window 76 through which light enters and exits probe 72. Window 76 includes one or more regions that include a fluorescent material. In one embodiment, the fluorescent material is a coating or film on a region of the window. In one embodiment, a region of the window is doped with the fluorescent material. In one embodiment, scanner 62 corresponds to scanner 120 of FIG. 4.

As shown, scanner 62 includes multiple light sources 64, 65, 66, 68. Each of the light sources may be or include one or more lasers and/or light emitting diodes (LEDs). Alternatively, other types of light sources may be used. While four light sources are shown, other numbers of light sources may be included in scanner 62. While light sources 64-68 are shown to be disposed in probe 72, they may alternatively be placed elsewhere in the scanner 62. Light sources 64, 66 may be non-coherent light sources, such as a white light source having a particular range of wavelengths that do not cause fluorescent material 78 to fluoresce. The non-coherent light sources 64, 68 may output light that is used to generate color images, such as color 2D images, of an imaged intraoral object. Light output by light sources 64, 66 may not cause fluorescent material 78 to fluoresce. Light source 65 may be a coherent light source that outputs light having particular wavelength that, when it is shined on fluorescent material 78, causes fluorescent material 78 to fluoresce. Light source 68 may be a coherent light source that outputs light having a particular wavelength that does not cause fluorescent material 78 to fluoresce. Light source 68 may emit light that is used to generate height maps of intraoral objects, and thus to determine a three-dimensional surface of intraoral objects. In one embodiment, light source 68 corresponds to semiconductor laser 128 of FIG. 4.

Scanner 62 may alternate between powering on light source 65, light source 68, and/or light sources 64, 66. In some embodiments, light source 65 is powered on at a beginning of scanning, such as when scanner 62 is activated, to detect the presence or absence of a sleeve thereon. During scanning, scanner 62 may alternate between use of light source 68 and one or more light sources 64, 66. As shown, light rays 70 emitted by light sources 64, 66 pass through window and fluorescent material 78 without causing the fluorescent material 78 to fluoresce. Similarly, light emitted by light source 68 does not cause fluorescent material to fluoresce. Thus, the fluorescent material does not negatively impact an ability of scanner 62 to accurately scan intraoral objects. Light rays 80 emitted by light source 65, on the other hand, cause fluorescent material 78 to fluoresce and emit light rays 82. The light rays 82 may be reflected back into probe 72 and detected by a detector.

The fluorescent material 78 and one or more of the light sources 64, 66, 68 may be selected such that wavelengths output by the light sources 64, 66, 68 do not cause the fluorescent material to fluoresce and such that wavelengths output by light source 65 does cause the fluorescent material to fluoresce. For example, fluorescent material 78 may be tuned to emit photons of a predetermined wavelength, e.g., at least 520 nm and/or less than 680 nm, or at least 410 nm and/or less than 700 nm, or within the visible spectrum of light. Some examples of fluorescent material that may be used include Alexa Fluor® 405, which has a maximum absorbance of around 401 nm and a maximum emission of around 421 nm, Alexa Fluor® 488, which has a maximum absorbance of around 495 nm and a maximum emission of around 519 nm, Alexa Fluor® 647, which has a maximum absorbance of around 650 nm and a maximum emission of around 665 nm, Alexa Fluor® 700, which has a maximum absorbance of around 702 nm and a maximum emission of around 723 nm, APC, which has a maximum absorbance of around 650 nm and a maximum emission of around 661 nm, Cy5, which has a maximum absorbance of around 649 nm and a maximum emission of around 670 nm, DyLight® 405, which has a maximum absorbance of around 400 nm and a maximum emission of around 420 nm, DyLight® 488, which has a maximum absorbance of around 493 nm and a maximum emission of around 518 nm, DyLight® 549, which has a maximum absorbance of around 562 nm and a maximum emission of around 576 nm, DyLight® 649, which has a maximum absorbance of around 654 nm and a maximum emission of around 673 nm, DyLight® 680, which has a maximum absorbance of around 692 nm and a maximum emission of around 712 nm, DyLight® 750, which has a maximum absorbance of around 752 nm and a maximum emission of around 778 nm, DyLight® 800, which has a maximum absorbance of around 777 nm and a maximum emission of around 794 nm, FITC, which has a maximum absorbance of around 490 nm and a maximum emission of around 525 nm, Pacific Blue™, which has a maximum absorbance of around 410 nm and a maximum emission of around 455 nm, PerCP, which has a maximum absorbance of around 490 nm and a maximum emission of around 675 nm, PE, which has a maximum absorbance of around 490 or 565 nm and a maximum emission of around 578 nm, Texas Red®, which has a maximum absorbance of around 596 nm and a maximum emission of around 615 nm, and TRITC, which has a maximum absorbance of around 596 nm and a maximum emission of around 570 nm. These are merely examples of fluorescent materials, and any other types of fluorescent materials may also be used.

It will be appreciated by persons skilled in the art that the present disclosure is not limited to what has been particularly shown and described hereinabove. Rather, the scope of the present disclosure includes both combinations and sub-combinations of the various features described hereinabove, as well as variations and modifications thereof that are not in the prior art, which would occur to persons skilled in the art upon reading the foregoing description.

What is claimed is:

1. An apparatus for intraoral scanning, the apparatus comprising:
    an elongate wand comprising a probe at a distal end of the elongate wand;
    one or more light projectors coupled to the elongate wand, the one or more light projectors configured to project light having a first wavelength;
    one or more cameras coupled to the elongate wand, each camera (a) comprising a camera sensor and objective optics comprising one or more lenses, and (b) configured to focus at an object focal plane that is located between 1 mm and 30 mm from a lens of the one or more lenses that is farthest from the camera sensor;
    a fluorescent transparent film deposited on a surface selected from the group consisting of: a window of the probe through which light exits and enters the probe, and a transparent surface that is not integral to the probe, wherein the fluorescent transparent film is configured to emit light having a second wavelength responsive to exposure to the projected light having the first wavelength; and
    a processor configured to run a three-dimensional image reconstruction algorithm based on the projected light and reflected light returning from an object exposed to the projected light to generate a three-dimensional surface of the object, wherein emitted light having the second wavelength is excluded from the three-dimensional image reconstruction algorithm.

2. The apparatus according to claim 1, wherein the one or more light projectors comprise one or more structured light projectors.

3. The apparatus according to claim 2, wherein each structured light projector comprises:
    (a) at least one laser diode;
    (b) a beam shaping optical element; and
    (c) a pattern generating optical element configured to generate a distribution of discrete unconnected spots of light at all planes located between 1 mm and 30 mm from the pattern generating optical element when the laser diode is activated to transmit light through the pattern generating optical element.

4. The apparatus according to claim 1, wherein the fluorescent transparent film comprises a layer of fluorescent ink deposited on the selected surface.

5. The apparatus according to claim 1, wherein the fluorescent transparent film comprises a layer of fluorescent polymer glued onto the selected surface.

6. The apparatus according to claim 5, wherein the layer of fluorescent polymer comprises a fluorescent polymer tape.

7. The apparatus according to claim 1, wherein the processor is further configured to identify fluorescence of the fluorescent transparent film in an image captured by at least one of the cameras and to filter out the emitted light caused by the fluorescence of the fluorescent transparent film.

8. The apparatus according to claim 7, wherein the selected surface is the transparent surface that is not integral to the probe.

9. The apparatus according to claim 8, wherein the processor is configured to determine whether the transparent surface is present by identifying fluorescence of the fluorescent transparent film.

10. The apparatus according to claim 9, wherein the processor is configured to set a focal depth of the one or more cameras in response to identified presence of the transparent surface.

11. The apparatus according to claim 8, wherein the transparent surface comprises a sleeve shaped and sized to be placed over the probe.

12. The apparatus according to claim 11, wherein the sleeve is rotationally asymmetric, and wherein the rotational asymmetry of the sleeve is such as to assist the sleeve in correctly being placed over the probe such that the transparent surface is aligned with the window of the probe.

13. The apparatus according to claim 11, wherein the probe and a distal end of the sleeve have the same shape.

14. The apparatus according to claim 8, wherein the fluorescent transparent film comprises a fluorescent barcode disposed on the transparent surface, and wherein the processor is configured to identify the transparent surface by identifying the fluorescence of the fluorescent barcode.

15. The apparatus according to claim 14, wherein the processor is configured to identify that the transparent surface has previously been used by identifying that the fluorescent barcode has previously been identified by the processor.

16. The apparatus according to claim 8, wherein the fluorescent transparent film is shaped to provide a fluorescent identifier disposed on the transparent surface, and wherein the processor is configured to identify the transparent surface by identifying the fluorescence of the fluorescent identifier.

17. The apparatus according to claim 16, wherein the processor is configured to identify that the transparent surface has previously been used, by identifying that the fluorescent identifier has previously been identified by the processor.

18. The apparatus of claim 1, further comprising:
a filter to filter out the emitted light having the second wavelength.

19. The apparatus of claim 1, wherein the emitted light having the second wavelength is excluded from the three-dimensional image reconstruction algorithm by the processor.

20. Apparatus for intraoral scanning, the apparatus comprising:
an elongate wand comprising a probe at a distal end of the elongate wand;
one or more light projectors coupled to the elongate wand, the one or more light projectors configured to project light having a first wavelength;
one or more cameras coupled to the elongate wand, each camera comprising a camera sensor and objective optics comprising one or more lenses;
a transparent window made of a fluorescent material, the transparent window selected from the group consisting of: a window of the probe through which light exits and enters the probe, and a window that is not integral to the probe, wherein the transparent window made of the fluorescent material is configured to emit light having a second wavelength responsive to exposure to the projected light having the first wavelength; and
a processor configured to run a three-dimensional image reconstruction algorithm based on the projected light and reflected light returning from an object exposed to the projected light to generate a three-dimensional surface of the object, wherein emitted light having the second wavelength is excluded from the three-dimensional image reconstruction algorithm.

21. The apparatus according to claim 20, wherein the one or more light projectors comprise one or more structured light projectors.

22. The apparatus according to claim 20, wherein the transparent window comprises a fluorescent glass filter.

23. The apparatus according to claim 20, wherein the processor is configured to identify fluorescence of the fluorescent material in an image captured by at least one of the cameras.

24. The apparatus according to claim 23, wherein the selected window is the window that is not integral to the probe.

25. The apparatus according to claim 24, further comprising a sleeve shaped and sized to be placed over the probe, and wherein the window is disposed in a wall of the sleeve.

26. The apparatus according to claim 24, wherein the processor is configured to determine whether the window is present by identifying fluorescence of the window.

27. The apparatus according to claim 26, wherein the processor is configured to set a focal depth of the one or more cameras in response to identified presence of the window.

28. The apparatus of claim 20, wherein each camera of the one or more cameras is configured to focus at an object focal plane that is located between 1 mm and 30 mm from a lens of the one or more lenses that is farthest from the camera sensor.

29. The apparatus of claim 20, further comprising:
a filter to filter out the emitted light having the second wavelength.

30. The apparatus of claim 20, wherein the emitted light having the second wavelength is excluded from the three-dimensional image reconstruction algorithm by the processor.

* * * * *